United States Patent
Joo et al.

(10) Patent No.: US 12,071,532 B2
(45) Date of Patent: Aug. 27, 2024

(54) BLUE LIGHT CUT FILM, OPTICAL FILTER COMPRISING SAME, AND DISPLAY DEVICE

(71) Applicant: LG CHEM, LTD., Seoul (KR)

(72) Inventors: Mun Kyu Joo, Daejeon (KR); Yeon Keun Lee, Daejeon (KR); Junhaeng Lee, Daejeon (KR); Deok Hwan Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1005 days.

(21) Appl. No.: 16/970,269

(22) PCT Filed: Oct. 31, 2019

(86) PCT No.: PCT/KR2019/014569
§ 371 (c)(1),
(2) Date: Aug. 14, 2020

(87) PCT Pub. No.: WO2020/091447
PCT Pub. Date: May 7, 2020

(65) Prior Publication Data
US 2021/0115225 A1    Apr. 22, 2021

(30) Foreign Application Priority Data
Oct. 31, 2018 (KR) .................. 10-2018-0131916

(51) Int. Cl.
```
C08K 5/56      (2006.01)
C07F 1/08      (2006.01)
C07F 15/04     (2006.01)
C08K 5/3492    (2006.01)
G02B 5/22      (2006.01)
```

(52) U.S. Cl.
CPC .................. *C08K 5/56* (2013.01); *C07F 1/08* (2013.01); *C07F 15/045* (2013.01); *C08K 5/3492* (2013.01); *G02B 5/223* (2013.01)

(58) Field of Classification Search
CPC .......... G02B 5/233; C09B 47/00–47/32; C07F 15/00–15/065
See application file for complete search history.

(56) References Cited

U.S. PATENT DOCUMENTS

| | | | |
|---|---|---|---|
| 9,971,191 B2 | 5/2018 | Cho et al. | |
| 2003/0194646 A1 | 10/2003 | Ogiso et al. | |
| 2008/0219011 A1 | 9/2008 | Sin et al. | |

FOREIGN PATENT DOCUMENTS

| | | |
|---|---|---|
| JP | 2003-057437 A | 2/2003 |
| JP | 2006-079011 A | 3/2006 |

(Continued)

OTHER PUBLICATIONS

Machine translation of JP2003-057437. Retrieved Jul. 12, 2023.*

(Continued)

*Primary Examiner* — Prashant J Khatri
(74) *Attorney, Agent, or Firm* — ROTHWELL, FIGG, ERNST & MANBECK, P.C.

(57) ABSTRACT

A blue light cut film including a diazaporphyrin-based compound of Chemical Formula 1, having absorption in a 380 nm to 450 nm range, and having a main absorption peak in a 560 nm to 600 nm range, wherein the main absorption peak has a full width at half the peak maximum of 30 nm or less.

14 Claims, 4 Drawing Sheets

(56) References Cited

FOREIGN PATENT DOCUMENTS

| JP | 2011-023322 A | 2/2011 | |
|---|---|---|---|
| JP | 2011-023323 A | 2/2011 | |
| JP | 2011-074161 A | 4/2011 | |
| JP | 2017-129849 A | 7/2017 | |
| KR | 10-2002-0093698 A | 12/2002 | |
| KR | 10-2016-0066707 A | 12/2014 | |
| KR | 10-2015-0039300 A | 4/2015 | |
| KR | 10-2015-0101106 A | 9/2015 | |
| KR | 10-2017-0034043 A | 3/2017 | |
| KR | 10-2017-0136746 A | 12/2017 | |
| WO | WO-9324849 A1 * | 12/1993 | ........... C08K 5/0091 |
| WO | 2009-031406 A1 | 3/2009 | |

OTHER PUBLICATIONS

International Search Report and Written Opinion issued for International Application No. PCT/KR2019/014569 on Feb. 7, 2020, 9 pages.
Matano et al., "Nickel(II) and Copper(II) Complexes of b-Unsubstituted 5, 15-Diazaporphyrins and Pyridazine-Fused Diazacorrinoids: Metal-Template Syntheses and Peripheral Functionalizations", Chemistry—A European Journal, 2012, 18, 6208-6216.
Yamaji, et al., "Carbolithiation of meso-aryl-substituted 5, 15-diazaporphyrin selectively provides 3-alkylated diazachlorins†", Chemial Communications, 2013, 49(44), 5064-5066.

* cited by examiner

[FIG. 1]
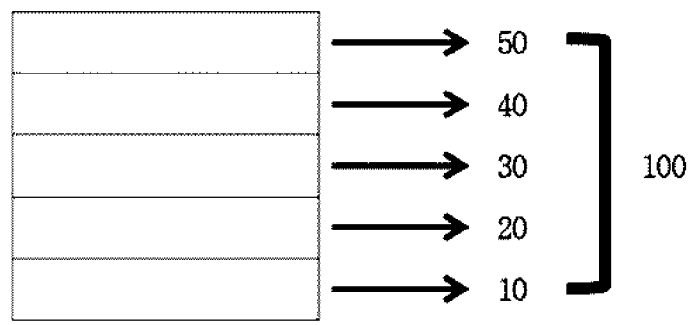
[FIG. 2]
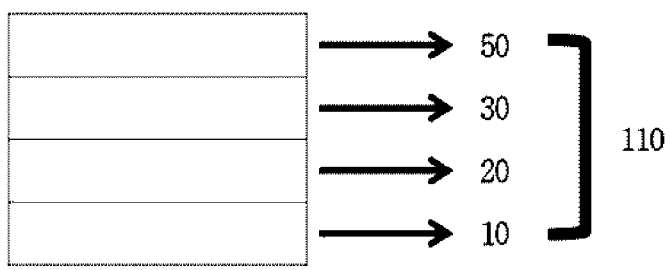
[FIG. 3]
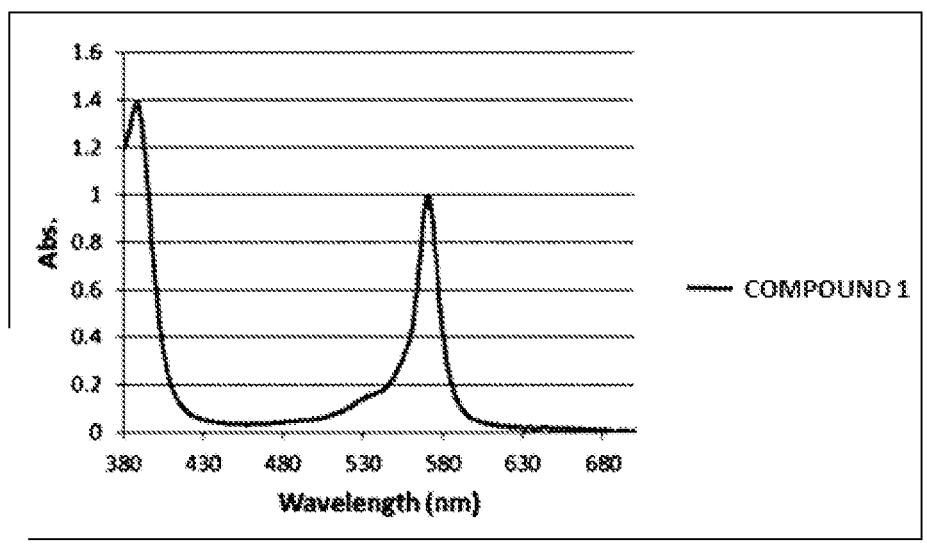

【FIG. 4】
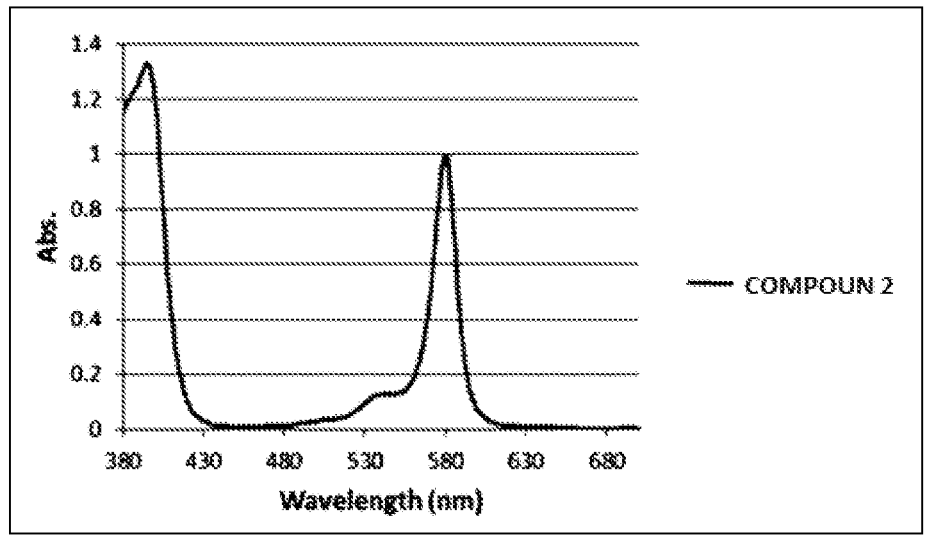
【FIG. 5】
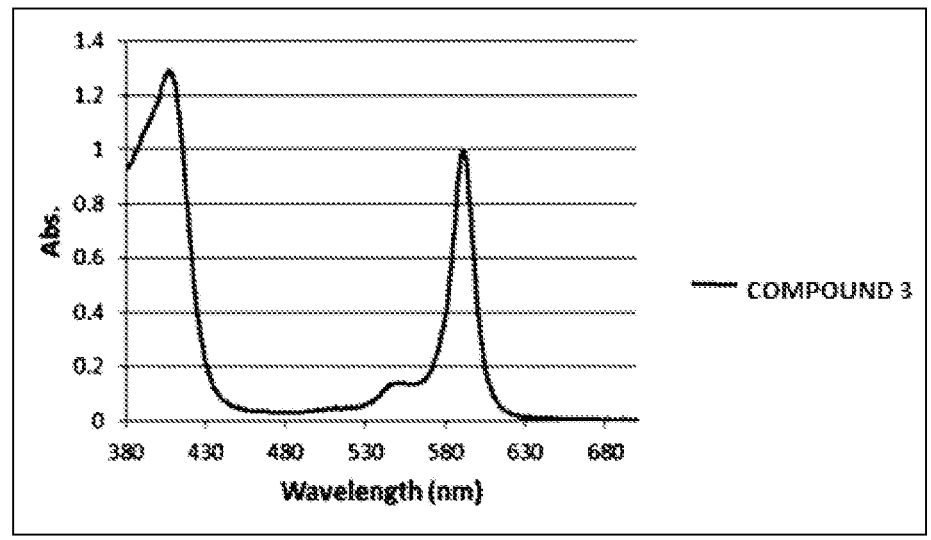

[FIG. 6]
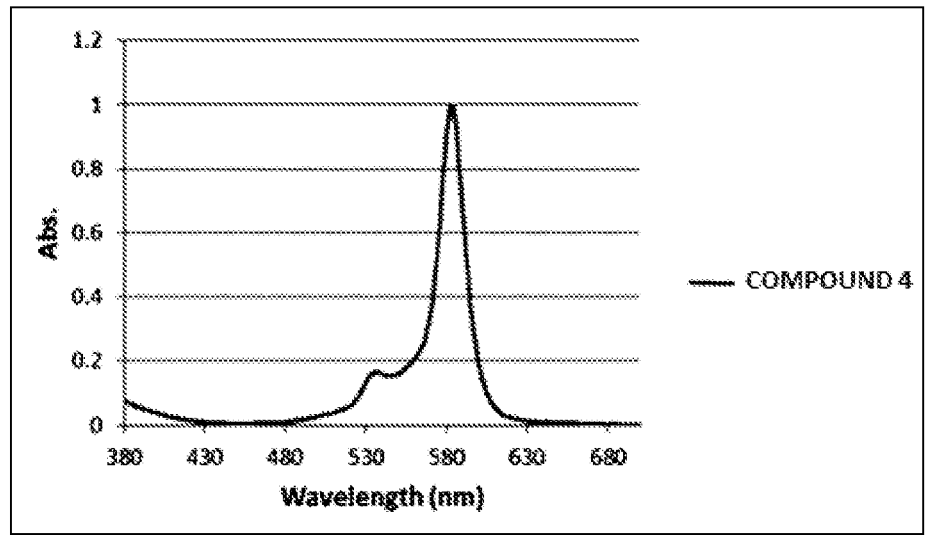
[FIG. 7]
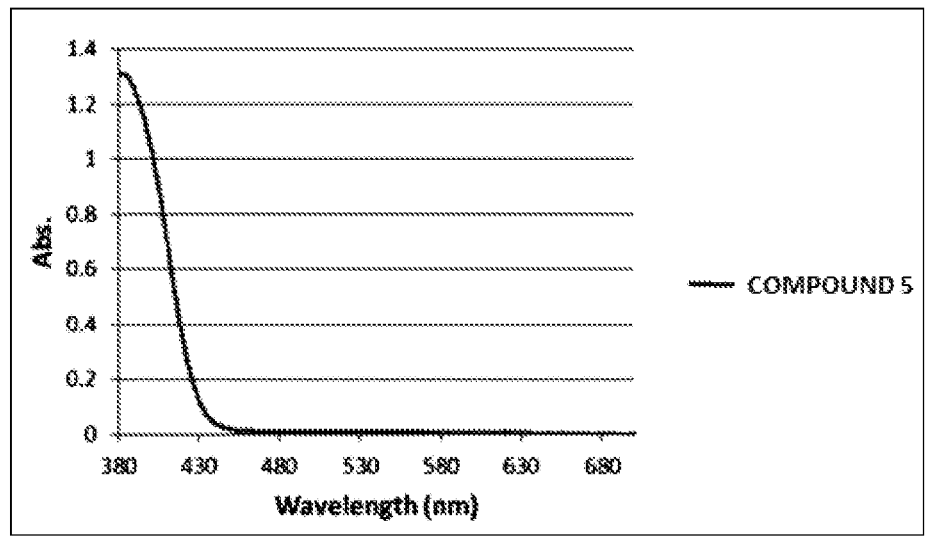

[FIG. 8]
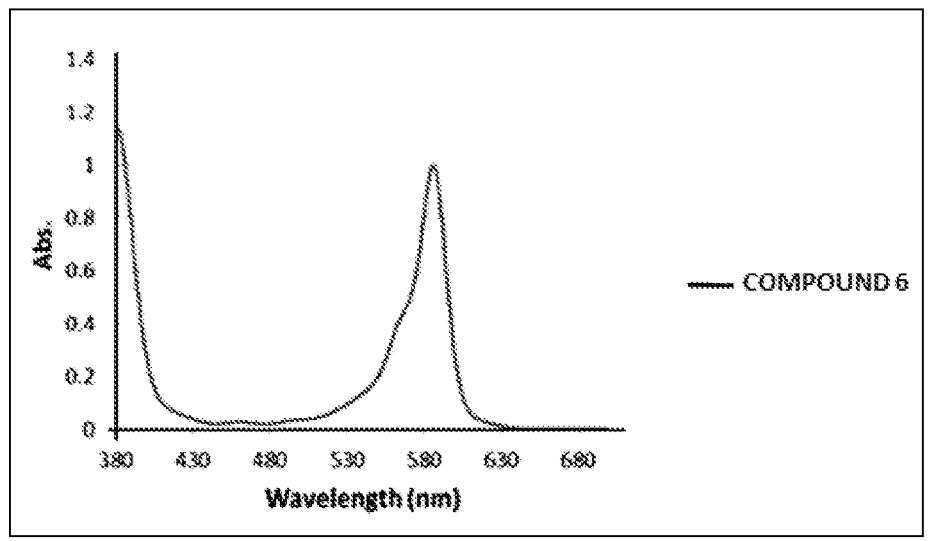
[FIG. 9]
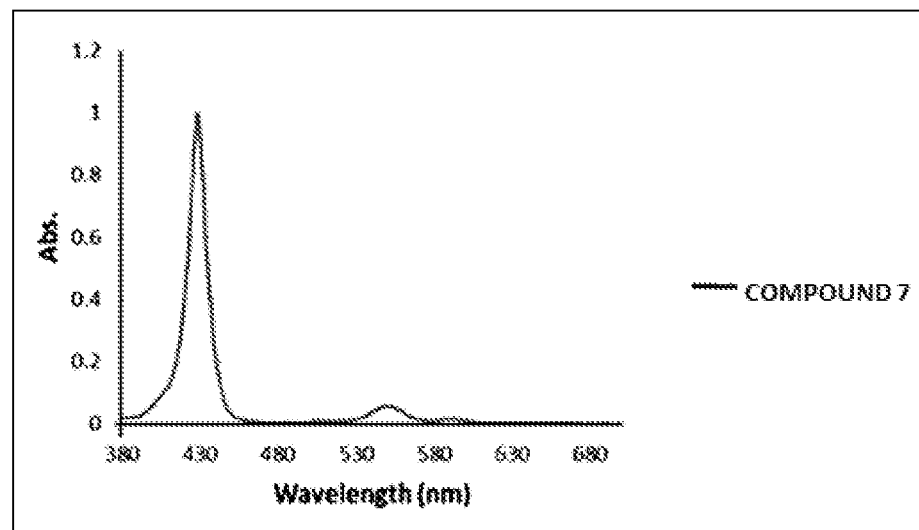

BLUE LIGHT CUT FILM, OPTICAL FILTER COMPRISING SAME, AND DISPLAY DEVICE

The present application is a 35 U.S.C. 371 National Phase Entry Application from PCT/KR2019/014569, filed on Oct. 31, 2019, designating the United States, which claims priority to and the benefits of Korean Patent Application No. 10-2018-0131916, filed with the Korean Intellectual Property Office on Oct. 31, 2018, the entire contents of which are incorporated herein by reference.

TECHNICAL FIELD

The present specification relates to a blue light cut film, and an optical filter and a display device including the same.

BACKGROUND OF THE INVENTION

Recently, there have been a growing awareness for importance of a blue light cut function in displays and lighting devices. Display devices such as smart watches, tablet PCs and smart glasses tend to be used outside more, and the importance has been growing along with UV cut materials.

Blue light is, among visible rays, blue light having a wavelength in a 380 nm to 495 nm range, and has the shortest wavelength among visible rays visible by the human eye, and has strong energy close to ultraviolet rays. Accordingly, when continuously exposed for a long period of time, performance of materials used in a display, a lighting device and the like declines shortening a product lifetime of the display or the lighting device. Particularly, light emitting materials used in an OLED display or an OLED lighting device are known to have low stability even in blue light, and therefore, a blue light cut function is very important.

In addition, when using a display in bright space, screen clearness is reduced due to light reflection, and therefore, an anti-reflection function is required. Particularly, in order to obtain an ability to express colors close to primary colors in a display, enhancement in the color gamut is also required. In a lighting device, obtaining high color rendering is required.

In order to obtain enhancement in all of such blue light cut, anti-reflection and color gamut, materials having respective functions are combined or filmed as a multilayer. However, there are problems in that a product becomes thick and costs increase, and therefore, studies to simplify a device structure has been required.

BRIEF DESCRIPTION OF THE INVENTION

The present specification is directed to providing a blue light cut film, and an optical filter and a display device including the same.

One embodiment of the present specification provides a blue light cut film including a diazaporphyrin-based compound of the following Chemical Formula 1, having absorption in a 380 nm to 450 nm range, and having a main absorption peak in a 560 nm to 600 nm range, wherein the main absorption peak has a full width at half maximum of 30 nm or less.

[Chemical Formula 1]

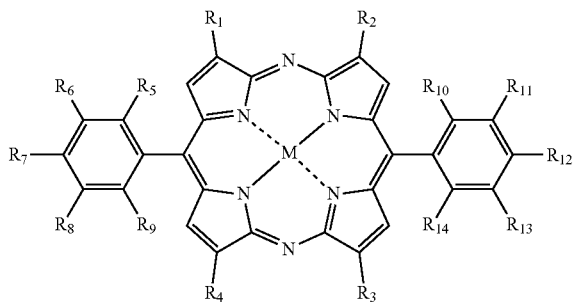

In Chemical Formula 1,
$R_1$ to $R_{14}$ are the same as or different from each other, and each independently hydrogen; a halogen group; a nitro group; a cyano group; an amino group; a carboxyl group; a hydroxyl group; a substituted or unsubstituted aryl group; a substituted or unsubstituted heteroaryl group; a substituted or unsubstituted alkyl group; or a substituted or unsubstituted alkoxy group, and
M is Cu; Ni; Pd; Mn; VO; or Pb.

Another embodiment of the present specification provides an optical filter including the blue light cut film described above.

Another embodiment of the present specification provides a display device including the optical filter described above.

Advantageous Effects

A display device according to one embodiment of the present specification is effective in enhancing color gamut while blocking blue light, and reducing external light reflectivity.

BRIEF DESCRIPTION OF DRAWINGS

FIG. 1 illustrates a display structure according to one embodiment of the present specification.

FIG. 2 illustrates a display structure not including a polarizing plate according to one embodiment of the present specification.

FIGS. 3 to 5 are absorption spectra of Examples 1 to 3 of the present specification.

FIGS. 6 to 9 are absorption spectra of Comparative Examples 1 to 4 of the present specification.

REFERENCE NUMERAL

10: Light Source
20: Color Filter
30: Blue Light Cut Film
40: Polarizing Plate
50: Protective Film
100: Display
110: Display Not Including Polarizing Plate

DETAILED DESCRIPTION OF THE INVENTION

Hereinafter, the present specification will be described in more detail.

In the present specification, a description of a certain part "including" certain constituents means capable of further including other constituents, and does not exclude other constituents unless particularly stated on the contrary.

In the present specification, a "main absorption peak" is a part performing a direct role in improving color gamut and external light reflectivity, and means a peak having the highest intensity (highest degree of absorption) in a visible region of 500 nm or greater.

In the present specification, a "full width at half maximum" represents a peak width in an absorption spectrum, and means a peak width at a value becoming half the peak maximum.

One embodiment of the present specification provides a blue light cut film including a diazaporphyrin-based compound, having absorption in a 380 nm to 450 nm range, and having a main absorption peak in a 560 nm to 600 nm range, wherein the main absorption peak has a full width at half maximum of 30 nm or less.

The meaning of having absorption in a 380 nm to 450 nm range is having absorption in all or some regions in a 380 nm to 450 nm range.

In the blue light cut film according to the present specification, an extinction coefficient (a) of the peak having maximum absorption in a 380 nm to 450 nm range needs to have a value of 105 cm- or greater, and the extinction coefficient (a) preferably has a value of 103 cm- or greater in all wavelengths in a 380 nm to 450 nm range. An upper limit of the extinction coefficient (a) in a 380 nm to 450 nm range is not limited, but may be, for example, $10^8$ cm$^{-1}$ or less.

In the present specification, the extinction coefficient ($\alpha$) may be analyzed through measuring an absorption spectrum, and herein, a Y axis of the absorption spectrum represents absorbance (A), and therefore, the extinction coefficient ($\alpha$) may be calculated by the following equation.

$$\text{Absorbance }(A) = \alpha bc = -\log T$$

$$\text{Extinction coefficient }(\alpha) = \frac{A}{bc} = \frac{-\log T}{bc}$$

(A: absorbance, $\alpha$: extinction coefficient, b: length (or thickness), c: concentration of dye, T: transmittance)

Most color filters currently in use do not include a blue light cut function, and generally do not have high absorption in a region of approximately 420 nm or less. On the other hand, the blue light cut film including a diazaporphyrin-based compound of the present disclosure is capable of obtaining low panel reflectivity and a blue light cut function while obtaining high color gamut, which is difficult to obtain when using only a color filter. In other words, by using only one material, the diazaporphyrin-based compound of the present disclosure, a multifunction may be obtained.

In one embodiment of the present specification, the diazaporphyrin-based compound is represented b the following Chemical Formula 1.

[Chemical Formula 1]

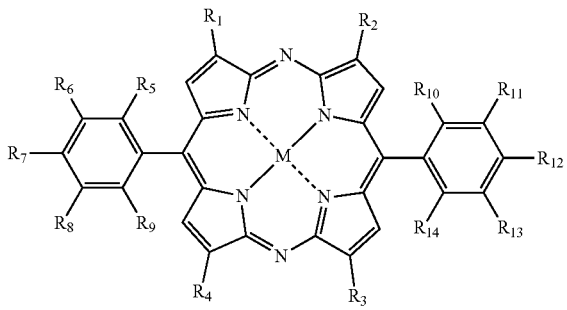

In Chemical Formula 1,
$R_1$ to $R_{14}$ are the same as or different from each other, and each independently hydrogen; a halogen group; a nitro group; a cyano group; an amino group; a carboxyl group; a hydroxyl group; a substituted or unsubstituted aryl group; a substituted or unsubstituted heteroaryl group; a substituted or unsubstituted alkyl group; or a substituted or unsubstituted alkoxy group, and
M is Cu; Ni; Pd; Mn; VO; or Pb.

By the diazaporphyrin-based compound according to the present disclosure having a structure in which the meso-C position is substituted with a phenyl group, an effect of improving light resistance stability of the diazaporphyrin-based compound is obtained.

In one embodiment of the present specification, Chemical Formula 1 may be represented by the following Chemical Formula 1-1.

[Chemical Formula 1-1]

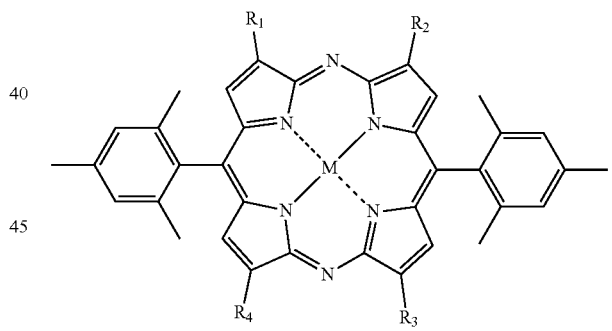

In Chemical Formula 1-1,
each substituent has the same definition as in Chemical Formula 1.

As in the compound of Chemical Formula 1-1, the diazaporphyrin structure requisitely has a mesityl group at the meso-C position, which may enhance light stability of the diazaporphyrin structure.

The diazaporphyrin-based compound according to one embodiment of the present specification is a metal complex, and no fluorescence is observed when forming a complex with M described above. Fluorescence is generally obtained from singlet transition, however, transition from singlet to triplet occurs in a metal complex due to a heavy atom effect. Herein, transition from triplet to singlet occurs as phosphorescence or non-luminescence extinction. In the metal complex of the diazaporphyrin-based compound, non-luminescence extinction occurs, and fluorescence disappears. On the other hand, existing materials having a blue light cut function formed only with organic materials mostly have properties of revealing fluorescence. Fluorescence may reduce a degree of polarity when using a polarizing plate, and, even when a polarizing plate is not used, may decrease color purity of a display.

When using a tetraazaporphyrin-based compound instead of the diazaporphyrin-based compound, absorption hardly occurs in a region of 380 nm or greater, and a porphyrin-based compound not including meso-N at all has sharp absorption in a blue absorption region, and thereby has a disadvantage of not having absorption in some blue regions or UVA wavelength regions.

The blue light cut film according to one embodiment of the present specification may block blue light from external light through absorption in a 380 nm to 450 nm range, and by having a main absorption peak in a 560 nm to 600 nm range, color gamut is enhanced, and reflectivity for external light decreases.

In one embodiment of the present specification, the main absorption peak of the blue light cut film has a full width at half maximum of 30 nm or less, preferably 25 nm or less, and more preferably nm or less. It is better as the main absorption peak has a smaller full width at half maximum, and for example, the full width at half maximum is 5 nm or greater.

In one embodiment of the present specification, the main absorption peak and the full width at half maximum may be measured using a UV-VIS spectrometer (SHIMADZU Corporation UV-3600 Plus).

In one embodiment of the present specification, the diazaporphyrin-based compound has absorption in a 380 nm to 450 nm range, has a main absorption peak in a 560 nm to 600 nm range, and the main absorption peak has a full width at half maximum of 25 nm or less.

In one embodiment of the present specification, the main absorption peak of the diazaporphyrin-based compound has a full width at half maximum of 25 nm or less, preferably 22 nm or less, and more preferably 20 nm or less. It is better as the main absorption peak has a smaller full width at half maximum, and for example, the full width at half maximum is 5 nm or greater.

In one embodiment of the present specification, the diazaporphyrin-based compound has a blue light cut function by absorbing light in a 380 nm to 450 nm range, and by having a main absorption peak in a 560 nm to 600 nm range, performs a role of enhancing color gamut, and reducing reflectivity for external light. In addition, high reliability for heat resistance and light resistance is provided by the metal complex structure.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one, two or more substituents selected from the group consisting of deuterium; a halogen group; an aryl group; an alkyl group; and an alkoxy group, or being substituted with a substituent linking two or more substituents among the substituents illustrated above, or having no substituents.

Examples of the substituents are described below, however, the substituents are not limited thereto.

In the present specification, examples of the halogen group may include fluorine, chlorine, bromine or iodine.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms.

In the present specification, the heteroaryl group includes S, O, Se, N or Si as a heteroatom, includes monocyclic or polycyclic having 2 to 60 carbon atoms, and may be further substituted with other substituents. According to one embodiment, the heteroaryl group has 2 to 60 carbon atoms.

In the present specification, the alkyl group may be linear or branched, and although not particularly limited thereto, the number of carbon atoms is preferably from 1 to 60. According to one embodiment, the alkyl group has 1 to 30 carbon atoms.

In the present specification, the alkoxy group may be linear, branched or cyclic. The number of carbon atoms of the alkoxy group is not particularly limited, but is preferably from 1 to 20.

In one embodiment of the present specification, $R_1$ to $R_4$ are the same as each other, and any one selected from the group consisting of hydrogen; an alkyl group having 1 to 10 carbon atoms; an alkoxy group having 1 to 10 carbon atoms; and an aryl group having 6 to 20 carbon atoms.

In one embodiment of the present specification, $R_1$ to $R_4$ are the same as each other, and any one selected from the group consisting of hydrogen; a halogen group; a methyl group; an ethyl group; a methoxy group; and a phenyl group.

According to one embodiment of the present specification, $R_6$, $R_8$, $R_{11}$, and $R_{13}$ are hydrogen.

According to one embodiment of the present specification, $R_5$, $R_7$, $R_9$, $R_{10}$, $R_{12}$ and $R_{14}$ are each an alkyl group having 1 to 10 carbon atoms.

According to another embodiment of the present specification, $R_5$, $R_7$, $R_9$, $R_{10}$, $R_{12}$ and $R_{14}$ are a methyl group.

In one embodiment of the present specification, M is Cu or Ni.

In one embodiment of the present specification, the blue light cut film may include two or more different types of the diazaporphyrin-based compound of Chemical Formula 1. When using a combination of two or more types of the diazaporphyrin-based compound, a blue light cut region (380 nm to 450 nm) and a color gamut improving region (560 nm to 600 nm) may be optimized. By combining the diazaporphyrin compounds having different blue light cut region and color gamut improving region, a blue light cut function may be effectively performed while minimizing a decrease in the luminance of a display considering a wavelength obtaining blue used in the display.

For example, in the diazaporphyrin-based compound represented by Chemical Formula 1, the diazaporphyrin-based compound in which $R_1$ to $R_4$ are substituted with hydrogen is classified as group 1, and the diazaporphyrin-based compound substituted with a halogen group is classified as group 2, and two types of the diazaporphyrin-based compound are combined to induce enhancement in the color gamut. Herein, the two types of the diazaporphyrin-based compound may be combined in a ratio of 7:3 to 3:7, and specifically 6:4 to 4:6.

In one embodiment of the present specification, the blue light cut film further includes at least one dye selected the group consisting of tetraazaporphyrin, cyanine and squalene series dyes. The above-described dyes are dyes having a main absorption peak in a 560 nm to 600 nm range, and when further provided in the blue light cut film, enhancement in the color gamut may be maximized.

A content of the at least one dye selected from the group consisting of tetraazaporphyrin, cyanine and squalene series dyes may be from 0.005 parts by weight to 4 parts by weight with respect to 100 parts by weight of the diazaporphyrin-based compound.

In one embodiment of the present specification, the blue light cut film may further include at least one dye selected firm the group consisting of benzotriazole, tris-resorcinol-triazine, hydroxy-benzotriazole and hydroxyphenyl-benzotriazole series dyes. The above-described dyes are dyes having a main absorption peak in a 380 nm to 450 nm range, and when further provided in the blue light cut film, a blue light cut function increases.

A content of the at least one dye selected from the group consisting of benzotriazole, tris-resorcinol-triazine, hydroxy-benzotriazole and hydroxyphenyl-benzotriazole series dyes may be from 0.001 parts by weight to 4 parts by weight with respect to 100 parts by weight of the diazaporphyrin-based compound.

In one embodiment of the present specification, the blue light cut film may further include an adhesive. The thickness of the blue light cut film including the adhesive may be from 15 μm to 25 μm, and preferably from 17 μm to 22 μm. When the thickness is in the above-mentioned range, a blue light cut function may be performed without affecting adhesion. Types of the adhesive are not limited, and for example, an acryl-based adhesive may be included.

In one embodiment of the present specification, the blue light cut film may further include a polymer resin. The polymer resin is preferably a thermoplastic polymer or a thermosetting polymer. Specifically, as a material of the resin matrix, poly(meth)acryl-based resins such as polymethyl methacrylate (PMMA), polycarbonate (PC)-based resins, polystyrene (PS)-based resins, polyarylene (PAR)-based resins, polyurethane (TPU)-based resins, styrene-acrylonitrile (SAN)-based resins, polysiloxane-based resins, polyvinylidene fluoride (PVDF)-based resins, modified polyvinylidene fluoride (modified-PVDF)-based resins and the like may be used. The thickness of the blue light cut film including the polymer resin is from 1 μm to 50 μm, more specifically from 3 μm to 50 μm, and preferably from 5 μm to 45 μm.

In one embodiment of the present specification, the blue light cut film further includes one or more types of an isocyanate-based crosslinking agent and a silane-based coupling agent.

In one embodiment of the present specification, an optical filter includes the blue light cut film. The optical filter may have optical filter constitutions known in the art except that it includes the above-described blue light cut film. For example, the optical filter may include a color filter, a polarizing plate and a protective film.

In one embodiment of the present specification, a display device includes the optical filter.

FIG. 1 illustrates a structure of the display (100) according to one embodiment of the present specification. Specifically, FIG. 1 illustrates a structure of the display including a light source (10), a color filter (20), a blue light cut film (30), a polarizing plate (40) and a protective film (50).

In one embodiment of the present specification, the display device may not include a polarizing plate.

FIG. 2 illustrates a structure of the display (110) not including a polarizing plate according to one embodiment of the present specification.

In one embodiment of the present specification, the display device may be a liquid crystal display device or an organic electroluminescent display device.

In one embodiment of the present specification, the display device may be included in, for example, TVs, computer monitors, laptops, mobile phones and the like.

Hereinafter, the present specification will be described in detail with reference to examples in order to specifically describe the present specification. However, the examples according to the present specification may be modified to various other forms, and the scope of the present specification is not to be construed as being limited to the examples described below. Examples of the present specification are provided in order to more fully describe the present specification to those having average knowledge in the art.

Example 1

A coating solution was prepared by adding 100 Parts by weight (solid content 15.3 parts by weight) of a butyl acrylate (BA)/hydroxyethyl methacrylate (HEMA) copolymer solution as an acryl-based adhesive, 0.05 parts by weight of the following Compound 1, 0.05 parts by weight of an isocyanate-based crosslinking agent (T-39) and 0.07 parts by weight of T-789J as a silane-based coupling agent to 45 parts by weight of methyl ethyl ketone (MEK) and mixing the result, and this was coated on a substrate film (PET) to a thickness of 20 μm to prepare a blue light cut film.

[Compound 1]

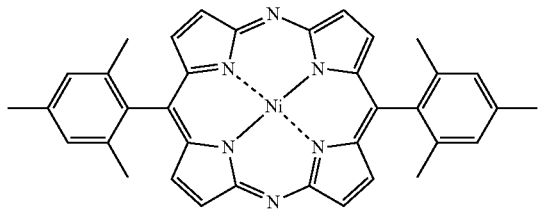

Example 2

A blue light cut film was prepared in the same manner as in Example 1 except that the following Compound 2 was used instead of Compound 1 in Example 1.

[Compound 2]

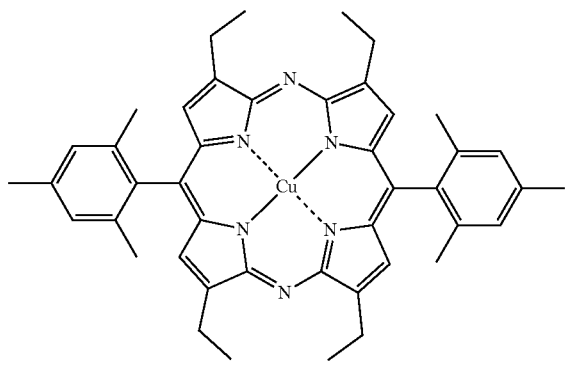

Example 3

A blue light cut film was prepared in the same manner as in Example 1 except that the following Compound 3 was used instead of Compound 1 in Example 1.

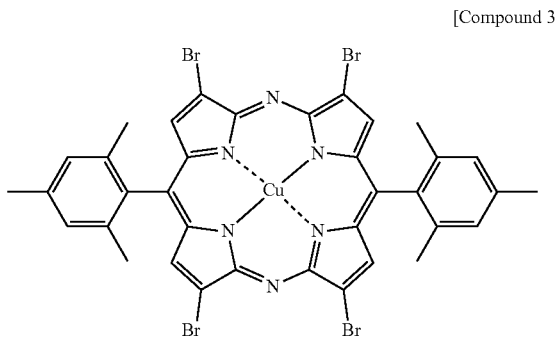
[Compound 3]

Comparative Example 1

A blue light cut film was prepared in the same manner as in Example 1 except that the following Compound 4 was used instead of Compound 1 in Example 1.

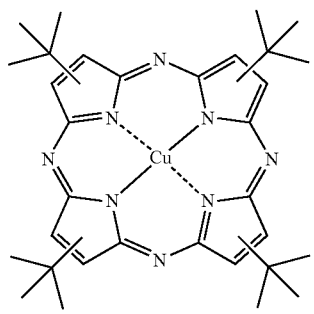
[Compound 4]

Comparative Example 2

A blue light cut film was prepared in the same manner as in Example 1 except that the following Compound 5 was used instead of Compound 1 in Example 1.

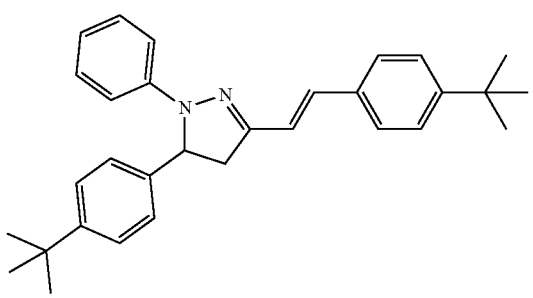
[Compound 5]

Comparative Example 3

A blue light cut film was prepared in the same manner as in Example 1 except that the following Compound 6 was used instead of Compound 1 in Example 1.

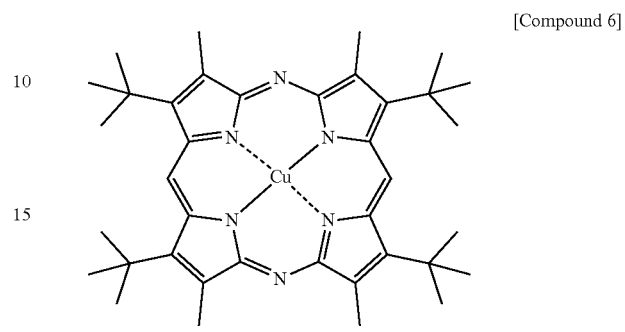
[Compound 6]

Comparative Example 4

A blue hg cut film was prepared in the same manner as in Example 1 except that the following Compound 7 was used instead of Compound 1 in Example 1.

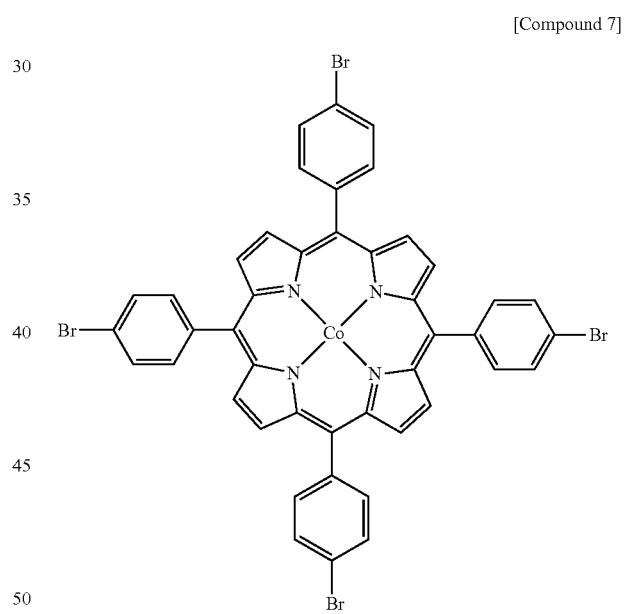
[Compound 7]

Compounds 1 to 3 were synthesized referring to synthesis methods of literatures of Chem. Eur. J. 2012, 18, 6208-6216 and Chem. Rev. 2017, 3138-3191, Compound 4 was synthesized referring to a synthesis method of a literature of Dyes and Pigments 2007, 73, 245-250, and Compound 5 was synthesized referring to US2010/0298573 A1. In addition, Compound 6 was synthesized using a method of J. Phys. Chem. 1997, 71, 7478, and Compound 7 was synthesized using a method of a literature of Phys. Chem. Chem. Phys., 2014, 16, 11209.

Experimental Example 1. Measurement of Absorption Spectrum

Results of measuring an absorption spectrum of each of the blue light cut films prepared in the examples and the comparative examples are shown in FIGS. 3 to 9, and the main absorption peak, the full width at half maximum and the presence of fluorescence revelation are shown in the following Table 1.

The absorption spectrum was measured using a UV-VIS spectrometer (SHIMADZU Corporation UV-3600 Plus), and the presence of fluorescence revelation and the spectrum maximum light emission wavelength were measured using a CMD2600D measuring device.

TABLE 1

|  | $\lambda_{max}$ (nm) | FWHM (nm) | Fluorescent Wavelength (nm) |
|---|---|---|---|
| Example 1 | 571 | 16 | X |
| Example 2 | 580 | 17 | X |
| Example 3 | 591 | 16 | X |
| Comparative Example 1 | 583 | 19 | X |
| Comparative Example 2 | — | — | 470 |
| Comparative Example 3 | 586 | 24 | X |
| Comparative Example 4 | 550 | 29 | X |

In Table 1, $\lambda_{max}$ is a wavelength having maximum absorption in a visible region of 500 nm or greater, FWHM is a full width at half maximum of the main absorption peak at 500 nm or greater in the absorption spectrum, and fluorescent wavelength is a maximum light emission wavelength of the revealed fluorescence.

Experimental Example 2. Analysis on Light Properties

In order to analyze optical properties of each of the blue light cut films prepared in the examples and the comparative examples, the blue light cut film was attached to an organic electroluminescent display panel, and the properties were compared.

As for the panel used in the measurement, each of the blue light cut films prepared in the examples and the comparative examples was attached to an organic electroluminescent display panel including a light emitting unit including an organic electroluminescent element, and a color filter (x, y colors of R, G and B are respectively (0.678, 0.319), (0.279, 0.587) and (0.138, 0.083)) to measure white light emission properties, and based on the measured color coordinates, color gamut was calculated in a DCI region of CIE 1976 Color Chromaticity Coordinates. The color coordinate was measured using SR-UL2, and light reflectivity was measured using a spectrometer (HR400) of Ocean Optics, Inc.

TABLE 2

|  | Light Transmittance (Absorption Region) | Color Gamut (DCI, %) | Reflectivity (@550 nm) (%) |
|---|---|---|---|
| Example 1 | 380 nm to 430 nm 500 nm to 600 nm | 85.7 | 3.4 |
| Example 2 | 380 nm to 440 nm 500 nm to 620 nm | 90.6 | 3.5 |
| Example 3 | 380 nm to 450 nm 530 nm to 630 nm | 92.6 | 3.4 |
| Comparative Example 1 | 500 nm to 630 nm | 92.2 | 3.4 |
| Comparative Example 2 | 380 nm to 450 nm | 84.5 | 5.6 |

TABLE 2-continued

|  | Light Transmittance (Absorption Region) | Color Gamut (DCI, %) | Reflectivity (@550 nm) (%) |
|---|---|---|---|
| Comparative Example 3 | 380 nm to 440 nm 500 nm to 630 nm | 92.5 | 3.4 |
| Comparative Example 4 | 390 nm to 460 nm 525 nm to 610 nm | 84.5 | 5.4 |

Experimental Example 3. Analysis on Light Stability

Each of the blue light cut films prepared in the examples and the comparative examples was attached to a polarizing plate, and after exposing the result for 500 hours using a Hg lamp (400 W), changes in the dye absorption were observed (Experimental Example 3-1), and after exposing a film without attaching a polarizing plate for 48 hours using a Hg lamp (400 W), changes in the dye absorption were observed (Experimental Example 3-2).

TABLE 3

|  | Changes in Transmittance (%) | |
|---|---|---|
|  | Experimental Example 3-1 | Experimental Example 3-2 |
| Example 1 | <1 | No Changes |
| Example 2 | <1 | No Changes |
| Example 3 | <1 | No Changes |
| Comparative Example 1 | <1 | No Changes |
| Comparative Example 2 | <3 | >5 |
| Comparative Example 3 | <3 | >3 |
| Comparative Example 4 | <1 | <2 |

From Tables 1 to 3, it was identified that Examples 1 to 3 had no revelation of fluorescence, had a blue light cut function through light absorption in a 380 nm to 450 nm region, and, through the light absorption with a full width at half maximum of 30 nm less in a 500 nm to 630 nm region and the color gamut measurement, had improved color gamut and reduced reflectivity for external light. In addition, it was seen that light stability was superior since where were almost no changes in the dye absorption by light.

On the other hand, it was seen that Comparative Example 1 using a tetraazaporphyrin-based compound had, although there was no fluorescence revelation problem and light stability was obtained, no blue light cut function since light absorption occurred only in a 500 nm to 630 nm region. Comparative Example 2 had light absorption in only a 380 nm to 450 nm region and a blue light cut function was obtained, however, it was identified that Comparative Example 2 was not effective in improving color gamut and external light reflectivity, had low light stability, and had a problem of fluorescence revelation. A problem of fluorescence revelation may reduce a degree of polarity when using a polarizing plate, and even when a polarizing plate is not used, color purity of a display may decrease. Comparative Example 3 has no fluorescence revelation by having a structure with no mesityl group present at the meso-C position of the diazaporphyrin structure, has a blue light cut function by having absorption in a 380 nm to 440 nm region, and may contribute to enhancement in the color gamut by having absorption in a 500 nm to 630 nm region, however, the use as a film having an effective blue light cut function is difficult since light stability by UV rays decreases. From such a result, it was seen that introducing a mesityl group at the meso-C position contributed to enhancing light stability of the diazaporphyrin structure. Comparative Example 4 is a porphyrin compound that does not include meso-N, and herein, it was seen that the compound was not able to contribute to enhancement in the color gamut since absorbance in a 500 nm to 600 nm region in the visible region significantly decreased, and it was difficult to effectively cut light in the UVA wavelength since absorption was not observed in a region of 390 nm or less.

The invention claimed is:

1. A blue light cut film comprising at least one diazaporphyrin-based compound represented by Chemical Formula 1-1,
wherein the blue light cut film has absorption in a 380 nm to 450 nm range, and a main absorption peak in a 560 nm to 600 nm range, and
wherein the main absorption peak has a full width at half the peak maximum of 30 nm or less, and
when observing changes in the dye absorption after exposing the blue light cut film without attaching a polarizing plate for 48 hours using a Hg lamp (400 W), no changes in the dye absorption are observed:

[Chemical Formula 1-1]

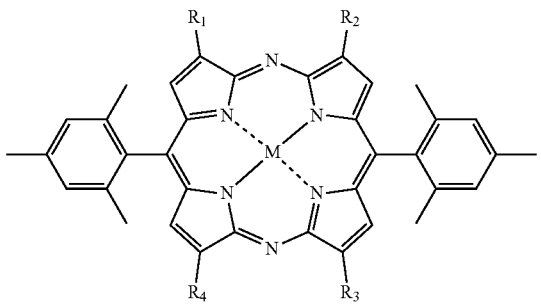

in the Chemical Formula 1-1,
$R_1$ to $R_4$ are the same as or different from each other, and each independently hydrogen; a halogen group; a nitro group; a cyano group; an amino group; a carboxyl group; a hydroxyl group; a substituted or unsubstituted aryl group; a substituted or unsubstituted heteroaryl group; a substituted or unsubstituted alkyl group; or a substituted or unsubstituted alkoxy group; and
M is Ni, Pd, Mn, VO, or Pb.

2. The blue light cut film of claim 1, wherein the diazaporphyrin-based compound has absorption in a 380 nm to 450 nm region, has a main absorption peak in a 560 nm to 600 nm region, and the main absorption peak has a full width at half the peak maximum of 25 nm or less.

3. The blue light cut film of claim 1, comprising two or more different diazaporphyrin-based compounds represented by Chemical Formula 1-1.

4. The blue light cut film of claim 1, further comprising at least one dye selected from tetraazaporphyrin, cyanine and squalene series dyes.

5. The blue light cut film of claim 4, wherein the at least one dye is included in an amount from 0.005 parts by weight to 4 parts by weight with respect to 100 parts by weight of the diazaporphyrin-based compound.

6. The blue light cut film of claim 1, further comprising at least one dye selected from benzotriazole, tris-resorcinol-triazine, hydroxy-benzotriazole and hydroxyphenyl-benzotriazole series dyes.

7. The blue light cut film of claim 6, wherein the at least one dye is included in an amount from 0.001 parts by weight to 4 parts by weight with respect to 100 parts by weight of the diazaporphyrin-based compound.

8. The blue light cut film of claim 1, further comprising an adhesive,
wherein a thickness of the blue light cut film is from 15 μm to 25 μm.

9. The blue light cut film of claim 1, further comprising a polymer resin,
wherein a thickness of the blue light cut film is from 1 μm to 50 μm.

10. An optical filter comprising the blue light cut film of claim 1.

11. A display device comprising the optical filter of claim 10.

12. The display device of claim 11, wherein the display device is a liquid crystal display device or an organic electroluminescent display device.

13. The blue light cut film of claim 9, wherein the polymer resin is a thermoplastic polymer or thermosetting polymer.

14. A blue light cut film comprising at least one diazaporphyrin-based compound represented by Chemical Formula 1-1,
wherein the blue light cut film has absorption in a 380 nm to 450 nm range, and has a main absorption peak in a 560 nm to 600 nm range, and
wherein the main absorption peak has a full width at half the peak maximum of 30 nm or less:

[Chemical Formula 1-1]

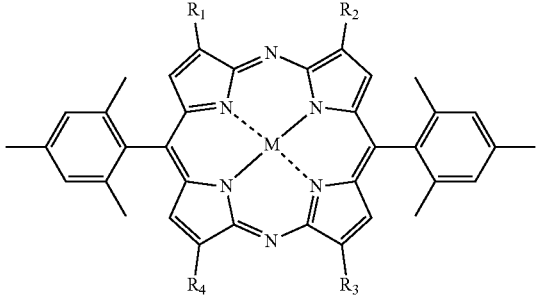

in the Chemical Formula 1-1,
$R_1$ to $R_4$ are the same as or different from each other, and each independently a halogen group; a nitro group; a cyano group; an amino group; a carboxyl group; a hydroxyl group; a substituted or unsubstituted aryl group; a substituted or unsubstituted heteroaryl group; a substituted or unsubstituted alkyl group; or a substituted or unsubstituted alkoxy group; and
M is Cu.

* * * * *